(12) United States Patent
Bender et al.

(10) Patent No.: US 9,517,979 B2
(45) Date of Patent: *Dec. 13, 2016

(54) PROCESS AND APPARATUS FOR THE PRODUCTION OF PARA-XYLENE

(71) Applicant: ExxonMobil Chemical Patents Inc.

(72) Inventors: Timothy P. Bender, Houston, TX (US); John R. Porter, Friendswood, TX (US); Dana L. Pilliod, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,298

(22) Filed: Dec. 15, 2015

(65) Prior Publication Data
US 2016/0272558 A1 Sep. 22, 2016

Related U.S. Application Data

(60) Provisional application No. 62/135,255, filed on Mar. 19, 2015.

(51) Int. Cl.
*C07C 5/27* (2006.01)
*B01J 19/24* (2006.01)

(52) U.S. Cl.
CPC .......... *C07C 5/2729* (2013.01); *B01J 19/2445* (2013.01); *C07C 5/2767* (2013.01); *B01J 2219/24* (2013.01)

(58) Field of Classification Search
CPC ....................................................... C07C 5/27
USPC ................................. 585/302, 304, 478, 477
See application file for complete search history.

(56) References Cited

U.S. PATENT DOCUMENTS 7,915,471 B2    3/2011   Leflaive et al.

FOREIGN PATENT DOCUMENTS

WO    WO2012058108    5/2012

OTHER PUBLICATIONS

U.S. Appl. No. 14/743,048, filed Jun. 18, 2015, Vander Pol et al.

*Primary Examiner* — Thuan D Dang (57) ABSTRACT

A process for producing para-xylene (PX) comprises supplying a hydrocarbon feed comprising xylenes and ethylbenzene (EB) to a PX recovery unit, where a PX-rich stream and at least one PX-depleted stream are recovered from the feed. The PX-depleted stream is then separated into an EB-rich stream and an EB-depleted stream in a divided wall column. The EB-depleted stream is then isomerized under at least partial liquid phase conditions to produce a first isomerized stream having a higher PX concentration than the PX-depleted stream, and the EB-rich stream is isomerized under at least partial vapor phase conditions to produce a second isomerized stream having a higher PX concentration than the PX-depleted stream. The first and second isomerized streams are then recycled to the PX recovery unit to recover additional PX and the process is repeated to define a so-called xylene isomerization loop.

19 Claims, 3 Drawing Sheets

PROCESS AND APPARATUS FOR THE PRODUCTION OF PARA-XYLENE

CROSS-REFERENCE OF RELATED APPLICATIONS

This application claims the benefit of Provisional Application No. 62/135,255, filed Mar. 19, 2015.

FIELD

This application relates to the treatment of ethylbenzene in the production of para-xylene.

BACKGROUND

Ethylbenzene (EB), para-xylene (PX), ortho-xylene (OX) and meta-xylene (MX) are often present together in $C_8$ aromatic product streams from chemical plants and oil refineries. Of these $C_8$ compounds, although high purity EB is an important raw material for the production of styrene, for a variety of reasons all high purity EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly(ethylene terephthalate), poly(propylene terephthalate), and poly (butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are a number of major technical challenges to be overcome in achieving this goal of maximizing PX yield. For example, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. A variety of methods are known to increase the concentration of PX in a $C_8$ aromatics stream. These methods normally involve cycling the stream between a separation step, in which at least part of the PX is recovered to produce a PX-depleted stream, and a xylene isomerization step, in which the PX content of the PX-depleted stream is returned back towards equilibrium concentration.

Figure 1:
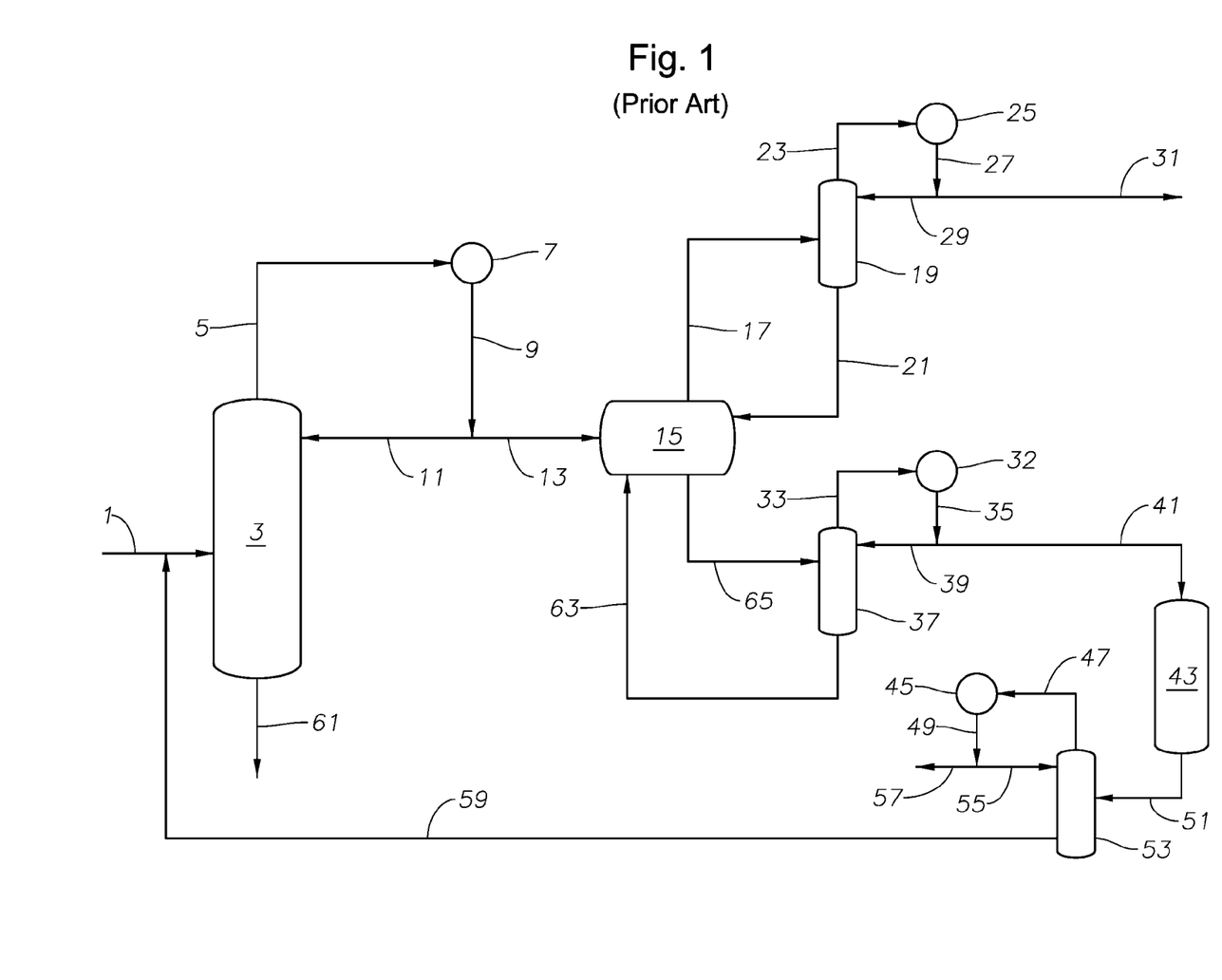
FIG. 1 is a flow diagram of a conventional para-xylene (PX) production and extraction process which employs liquid phase xylene isomerization and vapor phase xylene isomerization.

In a typical aromatics plant, such as that shown in FIG. 1, liquid feed, typically a $C_{8+}$ aromatic feedstream which has previously been processed by known methods to remove $C_{7-}$ species (particularly benzene and toluene), is fed by conduit 1 to xylenes re-run 3, an apparatus per se well known in the art. The xylenes re-run (or more simply a fractionation column) vaporizes the feed and separates the $C_8$ aromatics into an overhead mixture 5 of xylenes (OX, MX, and PX) and ethylbenzene (EB), and a bottom product 61 comprising $C_{9+}$ aromatics. The overhead mixture typically has a composition of about 40-50% metaxylene (MX), 15-25% PX, 15-25% OX, and 10-20% EB. Unless otherwise noted herein, percentages are % weight. The overhead is then condensed in condenser 7, an apparatus also per se well-known in the art, and becomes the feed for the PX recovery unit 15, via conduit 9 and 13, a portion of the condensed overhead may be returned to re-run 3 as reflux via conduits 9 and 11.

The PX recovery unit 15 may employ crystallization technology, adsorption technology, or membrane separation technology, each per se well known in the art. These technologies separate PX from its isomers and are capable of producing high purity PX up to 99.9%, which is taken from unit 15 via conduit 17. Shown in FIG. 1 is the case where unit 15 is an adsorptive separation unit, such as a Parex™ or Eluxyl™ unit, in which case typically the extract 17, which comprises a desorbent, such as paradiethylbenzene (PDEB), needs to be separated, such as by distillation, from the desired extract PX in distillation column 19, which generates an overhead 23 that is condensed in condenser 25 to yield a liquid stream 27, which is a high purity PX stream. This stream 27 may be taken off via conduit 31 and optionally a portion may be returned to column 19 as reflux via conduit 29. The desorbent is returned to the PX recovery system 15 via conduit 21. Raffinate from the recovery system 15, comprising MX, OX, EB, and some PX, is removed via conduit 65 and sent to unit 37, discussed below. Note: a portion of raffinate in 65 may be recovered and marketed as low-value solvent xylene.

The raffinate 65, which comprises mainly MX, OX, EB, and desorbent is sent to fractionation column 37, generating overhead 33 and bottoms 63. Overhead 33 contains MX, OX and EB, which is condensed in condenser 32 and sent via conduit 35 and then 41 to isomerization unit 43, discussed in more detail below. A portion may be returned to fractionator 37 via conduit 35 and then 39 as reflux. The desorbent in the bottoms product is returned to 15. Note that as used herein the term "raffinate" is used to mean the portion recovered from the PX recovery unit 15, whether the technology used is adsorptive separation, crystallization, or membrane, and then is sent to the isomerization unit 43, conventionally a vapor phase isomerization unit, which uses technology also per se well-known.

A stream consisting essentially of MX, OX and EB is sent to isomerization unit 43, an apparatus per se known in the art, to isomerize the MX and OX and optionally EB to PX. Isomerization unit 43 may be a vapor phase or liquid phase isomerization unit. Conventionally there are one or more heat exchangers or furnaces associated with the system shown in FIG. 1 between the PX recovery unit 15 and the isomerization unit that are not shown for convenience of view. Likewise, hydrogen separators and hydrogen compressors are also not shown for convenience of view. These and other features, such as valves and the like, would be apparent to one of ordinary skill in the art in possession of the present invention.

The product of the isomerization unit 43 is sent via conduit 51 to the $C_{7-}$ distillation tower 53, which separates the product of isomerization into a bottom stream 59 comprising equilibrium xylenes and the overhead 47, comprising $C_{7-}$ aromatics, e.g., benzene and toluene. The overhead product is condensed in condenser 45 and then the distribution of liquid product via conduit 49 may be apportioned as desired between conduit 57 and conduit 55, the former of which may be disposed of in numerous ways which would be well-known per se in the art, and the latter conduit returning $C_{7-}$ aromatics as reflux to tower 53. The bottoms product 59 of distillation tower 53 is then sent to xylenes re-run 3, either merging with feed 1 as shown in the figure, or it may be introduced by a separate inlet (not shown).

The xylene isomerization unit 43 may be conducted in either a vapor phase or liquid phase and is intended to accomplish two major things: isomerize the lower valued MX and OX to higher value PX, and convert EB into benzene/toluene and light gases (so-called "EB destruction") or optionally, isomerize EB to xylenes. Various options exist for using one or more of the xylenes isomerization technologies, but generally, conducting the xylene isomerization under at least partially liquid phase conditions minimizes xylene loss and is more energy efficient than vapor phase isomerization. However, under these conditions, little or none of the EB may be converted in the xylene isomerization step and as a result the amount of EB in the xylenes loop can build up to very high levels. Thus, to maximize the use of liquid phase isomerization, it is desirable to control the amount of EB in the PX-depleted stream subjected to liquid phase isomerization.

SUMMARY

The present invention is directed to a process for producing PX in which a hydrocarbon feed comprising xylenes and EB is provided to a PX recovery unit, which recovers a PX-rich stream and at least one PX-depleted stream. The at least one PX-depleted stream is sent to a divided wall column where it is separated into an EB-rich stream and an EB-depleted stream. At least a portion of the EB-depleted stream is isomerized at least partially in the liquid phase to produce a first isomerized stream having a higher PX concentration than the PX-depleted stream, and at least a portion of the EB-rich stream is isomerized at least partially in the vapor phase to produce a second isomerized stream having a higher PX concentration than the PX-depleted stream. The first and second isomerized streams are then recycled to the PX recovery unit. In one embodiment, the PX recovery unit produces a single PX-depleted stream, while in another embodiment, the PX recovery unit produces two PX-depleted streams—one rich in EB and one low in EB.

The invention further provides an apparatus for the production of PX comprising a PX recovery unit, which produces a PX-rich stream and at least one PX-depleted stream from a hydrocarbon feed, fluidly connected to a divided wall column in which the at least one PX-depleted stream is separated into an EB-rich stream and an EB-depleted stream; a liquid phase isomerization unit fluidly connected to the divided wall column to isomerize the EB-depleted stream and produce a first isomerized stream having a higher PX concentration than the PX-depleted stream; and a vapor phase isomerization unit fluidly connected to the divided wall column to isomerize the EB-rich stream and produce a second isomerized stream having a higher PX concentration than the PX-depleted stream. The apparatus may also include a xylenes fractionation column fluidly connected to the liquid phase isomerization unit, the vapor phase isomerization unit and the PX recovery unit, downstream of the liquid phase isomerization unit and the vapor phase isomerization unit and upstream of the PX recovery unit, and a fractionation column fluidly connected to the vapor phase isomerization unit and the xylenes fractionation column, downstream of the vapor phase isomerization unit and upstream of the xylenes fractionation column.

The present invention provides a process for controlling the amount of EB in the PX-depleted stream and maximizing the use of liquid phase isomerization, which minimizes xylene loss and results in energy savings.

DETAILED DESCRIPTION OF THE DRAWINGS

As used herein the term "$C_n$" hydrocarbon, wherein n is a positive integer, means a hydrocarbon having n number of carbon atom(s) per molecule. For example, a $C_8$ aromatic hydrocarbon means an aromatic hydrocarbon or mixture of aromatic hydrocarbons having 8 number of carbon atom(s) per molecule. The term "$C_n+$" hydrocarbon, wherein n is a positive integer, means a hydrocarbon having at least n number of carbon atom(s) per molecule, whereas the term "$C_n-$" hydrocarbon wherein n is a positive integer, means a hydrocarbon having no more than n number of carbon atom(s) per molecule.

Figure 2:
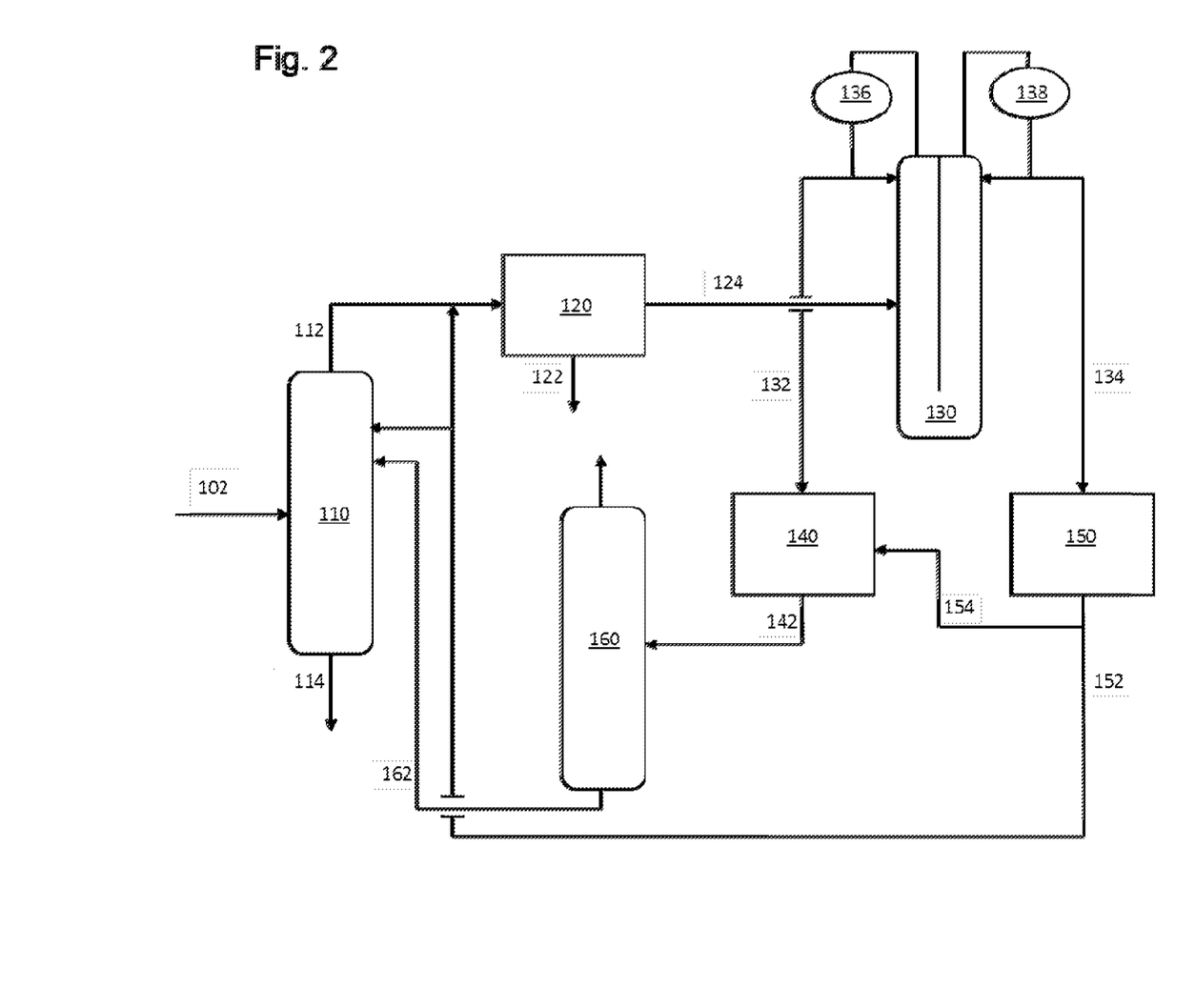
FIG. 2 is a flow diagram of one embodiment of the inventive process.

The present invention is an improved process for producing PX. With reference to FIG. 2, a hydrocarbon feed 102 comprising xylenes and EB is provided to a PX recovery unit 120, where a PX-rich stream 122 and at least one PX-depleted stream 124 are recovered from the feed. The PX-depleted stream 124 is then separated into an EB-rich stream 132 and an EB-depleted stream 134 in a divided wall column 130. At least part of the EB-depleted stream 134 is then fed to a xylene isomerization unit 150 where the EB-depleted stream 134 is isomerized under at least partial liquid phase conditions to produce a first isomerized stream 152 having a higher PX concentration than the PX-depleted stream 124. At least part of the EB-rich stream 132 is then fed to a xylene isomerization unit 140 where the EB-rich stream 132 is isomerized under at least partial vapor phase conditions to produce a second isomerized stream 142 having a higher PX concentration than the PX-depleted stream 124. At least part of the first and second isomerized streams 152, 142 are then recycled to the PX recovery unit 120 to recover additional PX and the process is repeated to define a so-called xylene isomerization loop.

Hydrocarbon Feed

The hydrocarbon feed 102 employed in the present process may be any hydrocarbon stream containing $C_8$ aromatic hydrocarbons, such as a reformate stream (product stream of a reformate splitting tower), a hydrocracking product stream, a xylene or EB reaction product stream, an aromatic alkylation product stream, an aromatic disproportionation stream, an aromatic transalkylation stream, a methanol to aromatic product stream, and/or a Cyclar™ process stream.

In one embodiment, the feed is the product of the alkylation of benzene and/or toluene with methanol and/or dimethyl ether in a methylation reactor. One such methylation reactor is described in U.S. Pat. Nos. 6,423,879 and 6,504,072, the entire contents of which are incorporated herein by reference, and employs a catalyst comprising a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa). The porous crystalline material may be a medium-pore zeolite, such as ZSM-5, which has been severely steamed at a temperature of at least 950° C. in the presence of at least one oxide modifier, for example including phosphorus, to control reduction of the micropore volume of the material during the steaming step. Such a methylation reactor is hereinafter termed a "PX-selective methylation reactor".

The feedstock may further comprise recycle stream(s) from the isomerization step(s) and/or various separating steps. The hydrocarbon feed comprises PX, together with meta-xylene (MX), ortho-xylene (OX), and ethylbenzene (EB). In addition to xylenes and EB, the hydrocarbon feedstock may also contain certain amounts of other aromatic or even non-aromatic compounds. Examples of such aromatic compounds are $C_{7-}$ hydrocarbons, such as benzene and toluene, and $C_9+$ aromatics, such as mesitylene, pseudocumene and others. These types of feedstream(s) are described in "Handbook of Petroleum Refining Processes", Eds. Robert A. Meyers, McGraw-Hill Book Company, Second Edition.

Para-Xylene Recovery

The hydrocarbon feed 102 is initially supplied to a PX recovery unit 120 to recover a PX-rich product stream 122 from the feed and leave a PX-depleted stream 124. In one embodiment, the PX-rich product stream 122 comprises at least 50 wt % PX, preferably at least 60 wt % PX, more preferably at least 70 wt % PX, even more preferably at least 80 wt % PX, most preferably at least 90 wt % PX, and ideally at least 95 wt % PX, based on the total weight of the PX rich product stream. The PX recovery unit 120 can include one or more of any of the PX recovery units known in the art, including, for example, a crystallization unit, an adsorption unit such as a PAREX™ unit or an ELUXYL™ unit, a reactive separation unit, a membrane separation unit, an extraction unit, a distillation unit, an extractive distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and the previously-mentioned "Handbook of Petroleum Refining Processes". In a preferred embodiment, the PX recovery unit 120 is a simulated moving bed adsorption unit such as a PAREX™ unit or an ELUXYL™ unit.

Depending on the composition of the hydrocarbon feed 102, one or more initial separation steps that serve to remove $C_{7-}$ and $C_9+$ hydrocarbons from the feed may occur prior to recovery of the PX-rich product stream 122. Generally the initial separation steps may include fractional distillation, crystallization, adsorption, a reactive separation, a membrane separation, extraction, or any combination thereof. In one embodiment, the feed 102 is passed through a xylenes fractionation tower 110 prior to passing to the PX recovery unit 120. The xylenes fractionation tower 110 produces an overhead stream 112 comprising $C_8$ hydrocarbons and a bottoms stream 114 containing $C_{9+}$ hydrocarbons.

In the embodiment shown in FIG. 2, the PX recovery unit 120 produces the conventional raffinate, or PX-depleted stream 124, comprising MX, OX and EB. In another embodiment, shown in FIG. 3, the PX recovery unit 120 may be modified to produce two different PX-depleted streams—a PX-depleted stream 126 rich in EB and a PX-depleted stream 128 low in EB. Examples of PX recovery units that produce multiple raffinate streams are described in U.S. patent application Ser. No. 14/624,861 and U.S. Pat. Nos. 7,582,206 and 8,030,533.

Divided Wall Column

Returning to FIG. 2, the PX-depleted stream 124 then passes to a divided wall column 130, which separates the PX-depleted stream 124 into two streams—an EB-rich stream 132 and an EB-depleted stream 134. The divided wall column 130 may be used in addition to, or, in a preferred embodiment, in place of, the raffinate tower (fractionator 37 in FIG. 1). As its name implies, the term "divided wall distillation column" refers to a particular known form of distillation column which comprises a dividing wall. The dividing wall vertically bisects a portion of the interior of the distillation column but does not extend either to the top or bottom sections of the column, thus, enabling the column to be refluxed and reboiled similar to a conventional column. The dividing wall provides a fluid impermeable baffle separating the interior of the column. The divided wall column may be configured for a number of processes, with an inlet to the column is located on one side of the dividing wall and one or more side draws are located on the opposing side, or an inlet on both sides of the divided wall column and multiple draws from the top or bottom of the column, or any combination thereof.

In a particular embodiment, the dividing wall extends from the top of the column down to a tray on which the EB concentration is low enough to provide an optimum ratio of low EB and high EB products, which is ascertainable by one skilled in the art using simulation tools. The PX-depleted stream 124 is provided to the column on one side of the dividing wall and the two streams are withdrawn from the top of the column. Each overhead stream is processed through a separate overhead product system 136, 138, each consisting of a condenser, which may be drumless, reflux pump, and an optional reflux drum. A portion of the EB-rich stream 132 may be returned to the divided wall column 130 as reflux, while the remainder of the EB-rich stream 132 is sent to isomerization unit 140. A portion of the EB-depleted stream 134 may be returned to the divided wall column 130 as reflux, while the remainder of the EB-depleted stream 134 is sent to isomerization unit 150. In other embodiments in which the amount of EB in the EB-rich stream is minimal, the EB-rich stream may be purged to fuel blending.

Figure 3:
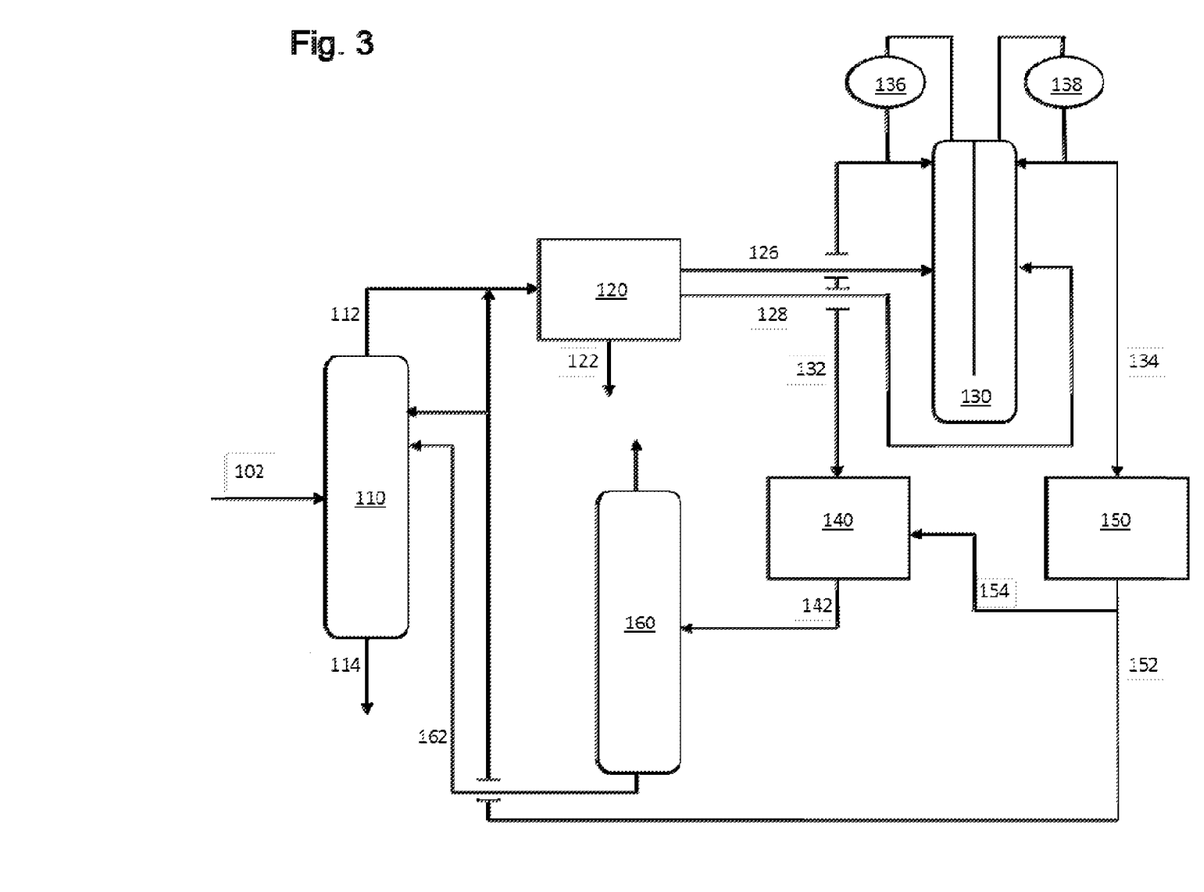
FIG. 3 is a flow diagram of a second embodiment of the inventive process.

In the embodiment depicted in FIG. 3, the PX-depleted stream 126 rich in EB enters the divided wall column 130 on one side of the dividing wall and the PX-depleted stream 128 low in EB enters the divided wall column 130 on the opposite side of the dividing wall. The divided wall column 130 further enhances the EB separation, and an EB-rich stream 132 and an EB-depleted stream 134 are recovered as overhead streams as in the previous embodiment. Using a divided wall column in conjunction with a simulated moving bed adsorption unit modified to separate the raffinate into high and low EB streams not only eliminates the need for the conventional raffinate tower, but the divided wall column provides additional EB separation beyond what the simulated moving bed adsorption unit achieves.

Xylene Isomerization

Because liquid phase isomerization converts little or none of the EB in the PX-depleted stream, in a preferred embodiment, the EB-depleted stream 134 is sent to isomerization unit 150, which is operated in the liquid phase, and the EB-rich stream 132 is sent to isomerization unit 140, which is operated in the vapor phase. Minimizing the amount of PX-depleted stream subjected to vapor phase isomerization saves energy and capital, as liquid phase isomerization requires less energy and capital than the vapor phase isomerization process due to the requirement of vaporizing the PX-depleted stream and the use of hydrogen, which requires an energy- and capital-intensive hydrogen recycle loop.

Liquid Phase Isomerization

The EB-depleted stream 134 is fed to a xylene isomerization unit 150 where the EB-depleted stream 134 is contacted with a xylene isomerization catalyst under at least partially liquid phase conditions effective to isomerize the PX-depleted, EB-depleted stream 134 back towards an equilibrium concentration of the xylene isomers. Suitable conditions for the liquid phase isomerization include a temperature of from about 200° C. to about 540° C., preferably from about 230° C. to about 310° C., and more preferably from about 270° C. to about 300° C., a pressure of from about 0 to 6895 kPa (g), preferably from about 1300 kPa (g) to about 3500 kPa (g), a weight hourly space velocity (WHSV) of from 0.5 to 100 $hr^{-1}$, preferably from 1 to 20 $hr^{-1}$, and more preferably from 1 to 10 $hr^{-1}$. Generally, the conditions are selected so that at least 50 wt % of the $C_8$ aromatics would be expected to be in the liquid phase.

Any catalyst capable of isomerizing xylenes in the liquid phase can be used in the xylene isomerization unit, but in one embodiment the catalyst comprises an intermediate pore size zeolite having a Constraint Index between 1 and 12. Constraint Index and its method of determination are described in U.S. Pat. No. 4,016,218, which is incorporated herein by reference. Particular examples of suitable intermediate pore size zeolites include ZSM-5, ZSM-11, ZSM-12, ZSM-22, ZSM-23, ZSM-35, ZSM-48, and MCM-22, with ZSM-5 and ZSM-11 being particularly preferred, specifically ZSM-5. It is preferred that the acidity of the zeolite, expressed as its alpha value, be greater than 300, such as greater than 500, or greater than 1000. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used to determine the alpha values cited herein include a constant temperature of 538° C. and a variable flow rate as described in detail in the Journal of Catalysis, Vol. 61, p. 395. A preferred catalyst is described in U.S. Pat. No. 8,569,559, which is incorporated herein by reference.

The product of the liquid phase xylene isomerization process 150 is a first isomerized stream 152 having a higher PX concentration than the PX-depleted, EB-depleted stream 134. The first isomerized stream 152 is then recycled to the PX recovery unit 120 to recover additional PX and the process is repeated to generate a so-called xylene isomerization loop. To manage the level of EB in the liquid phase isomerization loop and prevent a buildup of EB, a purge stream 154 may be removed from the first isomerized stream 152 at regular intervals (which may be determined by one skilled in the art) and passed to the xylene isomerization unit 140 where the EB may be converted.

Vapor Phase Isomerization

The EB-rich stream 132 is fed to a xylene isomerization unit 140 where the EB-rich stream 132 is contacted with a xylene isomerization catalyst under at least partially vapor phase conditions effective to isomerize the PX-depleted, EB-rich stream 132 back towards an equilibrium concentration of the xylene isomers. There are generally two types of vapor phase isomerization catalysts—one that isomerizes the four different C8 aromatic compounds, including EB, to their equilibrium concentrations and one that dealkylates EB to produce benzene and ethylene and isomerizes the xylene isomers. Either catalyst may be used for the vapor phase isomerization unit 140.

EB Isomerization

In one embodiment, the EB-rich stream 132 is subjected to EB isomerization to produce a stream containing the C8 aromatic compounds in equilibrium concentrations. The EB isomerization catalyst system comprises at least a first bed containing a xylene isomerization catalyst and a second bed downstream of the first bed and containing an ethylbenzene isomerization catalyst. The beds can be in the same or different reactors.

Typically, the xylene isomerization catalyst comprises an intermediate pore size molecular sieve having a Constraint Index within the approximate range of 1 to 12, such as ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). Alternatively, the xylene isomerization catalyst may comprise a molecular sieve selected from MCM-22 (described in U.S. Pat. No. 4,954,325); PSH-3 (described in U.S. Pat. No. 4,439,409); SSZ-25 (described in U.S. Pat. No. 4,826,667); MCM-36 (described in U.S. Pat. No. 5,250,277); MCM-49 (described in U.S. Pat. No. 5,236,575); and MCM-56 (described in U.S. Pat. No. 5,362,697), with MCM-49 being particularly preferred. The molecular sieve may also comprise a EUO structural type molecular sieve, with EU-1 being preferred, or mordenite. The entire contents of the above references are incorporated by reference herein.

The xylene isomerization catalyst may also include a hydrogenation/dehydrogenation component, which may be the same material present in the second, ethylbenzene isomerization catalyst, described below. If the same hydrogenation/dehydrogenation component is used in both catalysts, typically this component is present in a lower amount in the xylene isomerization catalyst than in the ethylbenzene isomerization catalyst. More preferably, however, to reduce its ethylbenzene conversion activity, the first catalyst composition does not contain a hydrogenation-dehydrogenation component.

In addition, it may be desirable to combine the molecular sieve of the xylene isomerization catalyst with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieve may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

Typically the xylene isomerization catalyst typically has an alpha value of about 4 to about 1000, such as from about 5 to about 80, with the preferred value being inversely dependent on reactor temperature.

The EB isomerization catalyst composition is primarily intended to isomerize the ethylbenzene in the feed selectively to para-xylene, while minimizing isomerization of the xylenes in the feed. The catalyst composition typically comprises a molecular sieve having unidimensional 10-membered ring pores. The phrase "unidimensional 10-membered ring pores" means that the pores of the molecular sieve are defined by 10-membered rings of tetrahedrally coordinated atoms which extend essentially in one dimension so that the pores are substantially free from any intersecting pores. Examples of suitable molecular sieves having unidimensional 10-membered ring pores include ZSM-5, ZSM-12, SAPO-11, ZSM-23, ZSM-22, NU-87, ZSM-11, ZSM-50, ZSM-57, SAPO-41, ZSM-48, EU-1, and mordenite. Preferred molecular sieves are ZSM-5, ZSM-12 or EU-1.

The molecular sieve of the catalyst composition typically has an alpha value of about 0.1 to about 20, for example from about 1 to about 5.

The molecular sieve used in the second catalyst composition is associated with a hydrogenation/dehydrogenation component. Examples of such components include the oxide, hydroxide, sulfide, or free metal (i.e., zerovalent) forms of Group VIII metals (i.e., Pt, Pd, Ir, Rh, Os, Ru, Ni, Co and Fe), Group VIB metals (i.e., Cr, Mo, W), Group IVA metals (i.e., Sn and Pb), Group VA metals (i.e., Sb and Bi), and Group VIIB metals (i.e., Mn, Tc and Re). Combinations of catalytic forms of such noble or non-noble metals, such as combinations of Pt with Sn, may be used. The metal is preferably in a reduced valence state. The reduced valence state of the metal may be attained, in situ, during the course of the reaction, when a reducing agent, such as hydrogen, is included in the feed to the reaction. Treatments such as coking or sulfiding may also be employed, especially at the start of a run with fresh catalyst, to modify the catalytic performance of the metal.

In one practical embodiment, the hydrogenation-dehydrogenation component is a noble metal (i.e., Pt, Pd, Ir, Rh, Os and Ru) and particularly is platinum. The amount of the hydrogenation-dehydrogenation component is suitably from about 0.001 to about 10 percent by weight, e.g., from about 0.03 to about 3 percent by weight, such as from about 0.2 to about 1 percent by weight of the total catalyst although this will, of course, vary with the nature of the component, with less of the highly active noble metals, particularly platinum, being required than of the less active base metals.

The EB isomerization catalyst composition may also include a binder and/or matrix material which may be the same as, or different from, any binder and/or matrix material contained by the first catalyst composition. In particular, the binder in the second catalyst composition may be a zeolitic material such that the second catalyst composition comprises a so-called "zeolite-bound zeolite" as described in, for example, U.S. Pat. No. 6,517,807, the entire contents of which are incorporated herein by reference. Thus, the second catalyst composition may comprise a core zeolite having unidimensional 10-membered ring pores, such as ZSM-48, bound with a high silica binder which is at least partly converted to a high silica zeolite (such as ZSM-5 or ZSM-48) which at least partly covers the surface of the core zeolite. By ensuring that the zeolitic binder has a higher silica to alumina molar ratio than the core zeolite, the binder can lower the surface activity of the core zeolite and hence reduce any unwanted xylene isomerization which would otherwise occur at the surface of the core zeolite.

In general, the EB isomerization catalyst composition is different from the xylenes isomerization catalyst composition, for example by containing a different molecular sieve, having a lower alpha value and/or by containing more or a more active hydrogenation/dehydrogenation component.

The conditions employed in the xylene isomerization stage of the process of the second embodiment are not narrowly defined but generally include a temperature of from 250 to about 600° C., a pressure of from about 0 to about 500 psig (100 to 3550 kPa), a weight hourly space velocity (WHSV) of between about 0.05 and about 50 hr-1, and a hydrogen, $H_2$, to hydrocarbon, HC, molar ratio of between about 0.05 and about 20.

The conditions used in the ethylbenzene isomerization stage are also not narrowly defined, but generally include a temperature of from about 250 to about 600° C., a pressure of from about 0 to about 500 psig (100 to 3550 kPa), a weight hourly space velocity (WHSV) of between about 0.01 and about 20 hr-1, and a hydrogen, $H_2$, to hydrocarbon, HC, molar ratio of between about 0.05 and about 20. Typically, the conditions include a temperature of from about 400 to about 500° C., a pressure of from about 50 to about 400 psig (445 to 2870 kPa), a WHSV of between about 1 and about 10 hr-1, and a $H_2$ to HC molar ratio of between about 1 and about 10.

In general, the xylene isomerization step and the ethylbenzene isomerization step of the present process are carried out in fixed bed reaction zones containing the catalyst compositions described above. The reaction zones may be in sequential beds in a single reactor, with the ethylbenzene isomerization catalyst being located downstream of the xylene isomerization catalyst and with the feed being cascaded from the first to the second bed without intervening separation of light gases. As an alternative, the ethylbenzene isomerization catalyst and the xylene isomerization catalyst can be disposed in separate reactors which, if desired, can be operated at different process conditions, in particular with the temperature of the ethylbenzene isomerization reactor being higher than that of the xylene isomerization reactor.

The product of the vapor phase xylene isomerization process 140 is a second isomerized stream 142 having a higher PX concentration than the PX-depleted, EB-rich stream 132. The second isomerized stream 142 is then recycled to the PX recovery unit 120 to recover additional PX and the process is repeated to generate a so-called xylene isomerization loop. In embodiments, the second isomerized stream 142 is passed through a detoluenizing fractionation column 160 to produce a $C_{7-}$ isomerized stream 164 and a $C_{8+}$ isomerized stream 162, which is passed through the xylenes re-run tower 110, before being recycled to the PX recovery unit 120 to recover additional PX.

EB Dealkylation

In another embodiment, the EB-rich stream 132 is subjected to xylenes isomerization in which the EB in the stream can be dealkylated to produce benzene. In this embodiment, where the ethylbenzene is removed by cracking/disproportionation, the para-xylene-depleted C8 stream is conveniently fed to a multi-bed reactor comprising at least a first bed containing an ethylbenzene conversion catalyst and a second bed downstream of the first bed and containing a xylene isomerization catalyst. The beds can be in the same or different reactors.

The ethylbenzene conversion catalyst typically comprises an intermediate pore size zeolite having a Constraint Index ranging from 1 to 12, a silica to alumina molar ratio of at least about 5, such as at least about 12, for example at least 20 and an alpha value of at least 5, such as 75 to 5000. Constraint Index and its method of determination are disclosed in U.S. Pat. No. 4,016,218, which is herein incorporated by reference, whereas the alpha test is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

Examples of suitable intermediate pore size zeolites include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); ZSM-58 (U.S. Pat. No. 4,417,780); EU-1; and mordenite. The entire contents of the above references are incorporated by reference herein. Preferred zeolites are ZSM-5, ZSM-12 or EU-1.

The zeolite employed in ethylbenzene conversion catalyst typically has a crystal size of at least 0.2 microns and exhibits an equilibrium sorption capacity for xylene, which can be either para, meta, ortho or a mixture thereof, of at least 1 gram per 100 grams of zeolite measured at 120° C. and a xylene pressure of 4.5±0.8 mm of mercury and an ortho-xylene sorption time for 30 percent of its equilibrium ortho-xylene sorption capacity of greater than 1200 minutes (at the same conditions of temperature and pressure). The sorption measurements may be carried out gravimetrically in a thermal balance. The sorption test is described in U.S. Pat. Nos. 4,117,026; 4,159,282; 5,173,461; and Re. 31,782, each of which is incorporated by reference herein.

The zeolite used in the ethylbenzene conversion catalyst may be self-bound (no binder) or may be composited with an inorganic oxide binder, with the zeolite content ranging from between about 1 to about 99 percent by weight and more usually in the range of about 10 to about 80 percent by weight of the dry composite, e.g., about 65% zeolite with about 35% binder. Where a binder is used, it is preferably non-acidic, such as silica. Procedures for preparing silica bound ZSM-5 are described in U.S. Pat. Nos. 4,582,815; 5,053,374; and 5,182,242, incorporated by reference herein.

In addition, the ethylbenzene conversion catalyst typically comprises from about 0.001 to about 10 percent by weight, e.g., from about 0.05 to about 5 percent by weight, e.g., from about 0.1 to about 2 percent by weight of a hydrogenation/dehydrogenation component. Examples of such components include the oxide, hydroxide, sulfide, or free metal (i.e., zero valent) forms of Group VIIIA metals (i.e., Pt, Pd, Ir, Rh, Os, Ru, Ni, Co, and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIIB metals (i.e., Ga and In), and Group IB metals (i.e., Cu, Ag and Au). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The metal may be in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The xylene isomerization catalyst employed in this embodiment typically comprises an intermediate pore size zeolite, e.g., one having a Constraint Index between 1 and 12, specifically ZSM-5. The acidity of the ZSM-5 of this catalyst, expressed as the alpha value, is generally less than about 150, such as less than about 100, for example from about 5 to about 25. Such reduced alpha values can be obtained by steaming. The zeolite typically has a crystal size less than 0.2 micron and an ortho-xylene sorption time such that it requires less than 50 minutes to sorb ortho-xylene in an amount equal to 30% of its equilibrium sorption capacity for ortho-xylene at 120° C. and a xylene pressure of 4.5+0.8 mm of mercury. The xylene isomerization catalyst may be self-bound form (no binder) or may be composited with an inorganic oxide binder, such as alumina. In addition, the xylene isomerization catalyst may contain the same hydrogenation/dehydrogenation component as the ethylbenzene conversion catalyst.

Using the catalyst system described above, ethylbenzene cracking/disproportionation and xylene isomerization are typically effected at conditions including a temperature of from about 400° F. to about 1,000° F. (204 to 538° C.), a pressure of from about 0 to about 1,000 psig (100 to 7000 kPa), a weight hourly space velocity (WHSV) of between about 0.1 and about 200 hr-1, and a hydrogen, H2 to hydrocarbon, HC, molar ratio of between about 0.1 and about 10. Alternatively, the conversion conditions may include a temperature of from about 650° F. and about 900° F. (343 to 482° C.), a pressure from about 50 and about 400 psig (446 to 2859 kPa), a WHSV of between about 3 and about 50 hr-1 and a H2 to HC molar ratio of between about 0.5 and about 5. The WHSV is based on the weight of catalyst composition, i.e., the total weight of active catalyst plus, if used, binder therefor.

The product of the vapor phase xylene isomerization process 140 is a second isomerized stream 142 having a higher PX concentration than the PX-depleted, EB-rich stream 132 and containing benzene. The second isomerized stream 142 is preferably processed through a detoluenizing fractionation 160 to produce a $C_{7-}$ isomerized stream 164 and a $C_{8+}$ isomerized stream 162, which is then recycled to the PX recovery unit 120 to recover additional PX.

Conducting xylenes isomerization under liquid phase conditions produces less $C_9$+ aromatics than xylenes isomerization under vapor phase conditions. Therefore, the first isomerized stream 152 may be provided to the xylenes fractionation tower 110 at a higher tray location than the second isomerized stream 142 or the $C_{8+}$ isomerized stream 162, yielding greater energy savings. Furthermore, a significant portion of the first isomerized stream 152 may bypass the xylenes fractionation tower 110 and directly enter the PX recovery unit 120, thereby saving energy by avoiding the re-fractionation altogether.

While the present invention has been described and illustrated by reference to particular embodiments, those of ordinary skill in the art will appreciate that the invention lends itself to variations and modification is not necessarily illustrated herein without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A process for producing para-xylene, the process comprising:
   (a) providing a hydrocarbon feed comprising para-xylene, meta-xylene, ortho-xylene, and ethylbenzene to a para-xylene recovery unit;
   (b) recovering a para-xylene-rich stream and at least one para-xylene-depleted stream from the hydrocarbon feed in the para-xylene recovery unit;
   (c) separating the at least one para-xylene-depleted stream into an ethylbenzene-rich stream, which contains a majority portion of the ethylbenzene from the at least one para-xylene-depleted stream, and an ethylbenzene-depleted stream, which contains a minor portion of the ethylbenzene from the at least one para-xylene-depleted stream, in a divided wall column;
   (d) isomerizing at least a portion of the ethylbenzene-depleted stream at least partially in the liquid phase back towards an equilibrium concentration of the xylenes isomers to produce a first isomerized stream having a higher para-xylene concentration than the para-xylene-depleted stream;
   (e) isomerizing meta-xylene, ortho-xylene, and ethylbenzene in at least a portion of the ethylbenzene-rich stream at least partially in the vapor phase back towards to an equilibrium concentration of xylene isomers to produce a second isomerized stream having a higher para-xylene concentration than the para-xylene-depleted stream; and
   (f) recycling at least a portion of the first and second isomerized streams to the para-xylene recovery unit.

2. The process of claim 1, wherein the para-xylene recovery unit comprises a simulated moving bed adsorption unit.

3. The process of claim 1, wherein step (e) is conducted under ethylbenzene dealkylation conditions.

4. The process of claim 1, wherein step (e) is conducted under ethylbenzene isomerization conditions.

5. The process of claim 1, wherein two para-xylene-depleted streams are recovered from the para-xylene recovery unit in step (b), a para-xylene-depleted stream rich in ethylbenzene and a para-xylene-depleted stream low in ethylbenzene.

6. The process of claim 1, wherein the hydrocarbon feed is selected from the group consisting of a reformate stream, a hydrocracking product stream, a xylene or EB reaction product stream, an aromatic alkylation product stream, an aromatic disproportionation stream, and mixtures thereof.

7. The process of claim 1, wherein the hydrocarbon feed comprises a benzene and/or toluene methylation product stream.

8. The process of claim 1, further comprising separating a $C_{7-}$ isomerized stream from the second isomerized stream in a fractionation column prior to step (f).

9. The process of claim 1, further comprising separating the first and second isomerized streams into an overhead stream comprising $C_8$ hydrocarbons and a bottoms stream containing $C_{9+}$ hydrocarbons in a xylenes fractionation column prior to step (f).

10. The process of claim 9, wherein the first isomerized stream is provided to the xylenes fractionation column at a higher location than the second isomerized stream.

11. A process for producing para-xylene, the process comprising:
   (a) providing a hydrocarbon feed comprising para-xylene, meta-xylene, ortho-xylene, and ethylbenzene to a para-xylene recovery unit;
   (b) recovering a para-xylene-rich stream, a para-xylene-depleted stream rich in ethylbenzene and a para-xylene-depleted stream low in ethylbenzene from the feed in the para-xylene recovery unit;
   (c) separating the para-xylene-depleted stream rich in ethylbenzene and para-xylene-depleted stream low in ethylbenzene into an ethylbenzene-rich stream, which contains a majority portion of the ethylbenzene from the at least one para-xylene-depleted stream, and an ethylbenzene-depleted stream, which contains a minor portion of the ethylbenzene from the at least one para-xylene-depleted stream, in a divided wall column;
   (d) isomerizing at least a portion of the ethylbenzene-depleted stream at least partially in the liquid phase back towards an equilibrium concentration of the xylenes isomers to produce a first isomerized stream having a higher para-xylene concentration than the para-xylene-depleted stream;
   (e) isomerizing meta-xylene, ortho-xylene, and ethylbenzene in at least a portion of the ethylbenzene-rich stream at least partially in the vapor phase back towards to an equilibrium concentration of xylene isomers to produce a second isomerized stream having a higher para-xylene concentration than the para-xylene-depleted stream; and
   (f) recycling at least a portion of the first and second isomerized streams to the para-xylene recovery unit.

12. The process of claim 11, wherein the para-xylene recovery unit comprises a simulated moving bed adsorption unit.

13. The process of claim 11, wherein step (e) is conducted under ethylbenzene dealkylation conditions.

14. The process of claim 11, wherein step (e) is conducted under ethylbenzene isomerization conditions.

15. The process of claim 11, wherein the hydrocarbon feed is selected from the group consisting of a reformate stream, a hydrocracking product stream, a xylene or EB reaction product stream, an aromatic alkylation product stream, an aromatic disproportionation stream, an aromatic transalkylation stream, a methanol to aromatic product stream, and mixtures thereof.

16. The process of claim 11, wherein the hydrocarbon feed comprises a benzene and/or toluene methylation product stream.

17. The process of claim 11, further comprising separating a $C_{7-}$ isomerized stream from the second isomerized stream in a detoluenizing fractionation column prior to step (f).

18. The process of claim 11, further comprising separating the first and second isomerized streams into an overhead stream comprising $C_8$ hydrocarbons and a bottoms stream containing $C_{9+}$ hydrocarbons in a xylenes fractionation column prior to step (f).

19. The process of claim 18, wherein the first isomerized stream is provided to the xylenes fractionation column at a higher location than the second isomerized stream.

* * * * *

UNITED STATES PATENT AND TRADEMARK OFFICE
CERTIFICATE OF CORRECTION

PATENT NO. : 9,517,979 B2  
APPLICATION NO. : 14/969298  
DATED : December 13, 2016  
INVENTOR(S) : Timothy P. Bender, John R. Porter and Dana L. Pilliod It is certified that error appears in the above-identified patent and that said Letters Patent is hereby corrected as shown below:

In the Claims

At Column 13, Line 59, Claim 6 add --an aromatic transalkylation stream, a methanol to aromatic product stream,-- before "and mixtures thereof."

Signed and Sealed this  
Twenty-fifth Day of April, 2017

Michelle K. Lee  
*Director of the United States Patent and Trademark Office*